United States Patent
Weitekamp et al.

(10) Patent No.: US 6,882,429 B1
(45) Date of Patent: Apr. 19, 2005

(54) TRANSVERSE OPTICAL FIBER DEVICES FOR OPTICAL SENSING

(75) Inventors: Daniel P. Weitekamp, Altadena, CA (US); Louis A. Madsen, Los Angeles, CA (US)

(73) Assignee: California Institute of Technology, Pasadena, CA (US)

( * ) Notice: Subject to any disclaimer, the term of this patent is extended or adjusted under 35 U.S.C. 154(b) by 592 days.

(21) Appl. No.: 09/575,709

(22) Filed: Jul. 20, 2000

Related U.S. Application Data
(60) Provisional application No. 60/144,745, filed on Jul. 20, 1999.

(51) Int. Cl.$^7$ ............................................... G01B 7/02
(52) U.S. Cl. ...................................................... 356/482
(58) Field of Search .............................. 356/477, 479, 356/482, 501, 521, 498; 250/227.19, 227.27; 324/95, 96, 97, 224.1; 385/30–43

(56) References Cited

U.S. PATENT DOCUMENTS

| | | | | |
|---|---|---|---|---|
| 4,516,073 A | * | 5/1985 | Doriath et al. | 324/244.1 |
| 5,017,010 A | | 5/1991 | Mamin et al. | |
| 5,253,312 A | * | 10/1993 | Payne et al. | 385/31 |
| 5,321,501 A | | 6/1994 | Swanson et al. | |
| 5,381,229 A | * | 1/1995 | Murphy et al. | 356/477 |
| 5,459,570 A | | 10/1995 | Swanson et al. | |
| 5,953,477 A | * | 9/1999 | Wach et al. | 385/115 |
| 5,982,009 A | * | 11/1999 | Hong et al. | 257/414 |
| 6,671,055 B1 | * | 12/2003 | Wavering et al. | 356/478 |

OTHER PUBLICATIONS

Tearney et al., "In Vivo Endoscopic Optical Biopsy with Optical Coherence Tomography," Science, vol. 276, pp. 2037–2039, Jun. 27, 1997.

Yasseen et al., "A Rotary Electrostatic Micromotor 1×8 Optical Switch," IEEE Journal of Selected Topics in Quantum Electronics, vol. 5, No. 1, pp. 26–32, Jan./Feb. 1999.

Ilchenko et al, 'Pigtailing the high–Q microsphere cavity: a simple fiber coupler for optical whispering–gallery modes', Optics Letters, pps. 723–725, vol. 24, No. 10, May 15, 1999.

Kenny et al. 'Micromachined silicon tunnel sensor for motion detection', Applied Physics Letters, pps. 100–102, vol. 58, No. 1, Jan. 7, 1991.

Rugar et al., 'Improved fiber–optic interferometer for atomic force microscopy', Applied Physics Letters, pps. 2588–2590, vol. 55, No. 25, Dec. 18, 1989.

Namkung et al., 'FT–IR Optical Fiber Remote Detection of Aluminum Hydroxide by Evanescent Wave Absorption Spectroscopy', Applied Spectroscopy, pps. 1305–1310.

Tai et al., 'Fiber–optic evanescent–wave methane–gas sensor using optical absorption for the 3.392–$\mu$m line of a He–Ne laser', Optics Letters, pps. 437–439, vol. 12, No. 6, Jun. 1987.

Hale et al., 'Demonstration of an optimized evanescent field optical fibre sensor', Analytica Chimica Acta, pps. 49–54, vol. 293, No. 1–2, Jul. 20, 1994.

Hale et al., 'Fluorescent sensors based on tapered single–mode optical fibres', Sensors and Actuators, pps. 233–240.

Jeunhomme, 'Single–Mode Fiber Optics', p. 10, Marcel Dekker, Inc., New York, 1983.

'Fiber Optic Sensors', Ed. By Eric Udd, pps. 289–304, John Wiley, New York, 1991.

Jin et al., 'A liquid contamination detector for D–fibre sensors using white light interferometry', Measurement Science & Technology, pps. 1471–1475, 1995.

* cited by examiner

Primary Examiner—Samuel A. Turner
Assistant Examiner—Michael A. Lyons
(74) Attorney, Agent, or Firm—Fish & Richardson P.C.

(57) ABSTRACT

Techniques and devices using a fiber to couple light efficiently and compactly in a direction transverse to the fiber core for optical sensing, optical switching, and optical data storage applications. Devices are described for all-fiber optical switching, multiple-disk high-data-rate optical disk drives with compact optical fiber read/write heads, compact fiber-optic interferometers for position, measurements, and endoscopic probes for medical tissue modification and measurement.

8 Claims, 9 Drawing Sheets

TRANSVERSE OPTICAL FIBER DEVICES FOR OPTICAL SENSING

CROSS REFERENCE TO RELATED APPLICATIONS

Continuity Statement

This application claims the benefit of U.S. Provisional Application No. 60/144,745, filed Jul. 20, 1999.

BACKGROUND OF INVENTION

This application relates to optical fiber devices, and more specifically, to devices and sensing techniques using optical fibers to couple radiation energy.

Optical fibers can be used to guide and transmit optical signals. An optical fiber may include a high-index fiber core surrounded by a lower-index fiber cladding. This structure can confine the majority of energy of a guided optical mode within the fiber core and guide the optical energy to propagate along the fiber core through total internal reflections at the boundary of the fiber core and the fiber cladding. One method of coupling an optical signal into and out of a fiber is coupling along the fiber core axis. One distal end of the fiber may have a polished facet normal to the fiber axis to allow transmission of light out of the fiber along the longitudinal direction of the fiber core.

Since a fiber is compact in size and is mechanically flexible, it can be deployed in various environments to deliver and receive light where traditional light-guiding optical elements may be inconvenient or even infeasible. For example, a fiber may be directly coupled to a semiconductor diode or a semiconductor substrate containing optoelectronic circuits to receive light and deliver the received light to a desired destination. A fiber with an oblique-angle-polished end facet has been used to couple optical energy via evanescent fields through the angle-polished facet. See Ilchenko et. al., Optics Letters, vol. 24(11), pp. 723, 1999.

Optical fibers can also function as probes to collect optical signals for various sensing purposes. For example, a fiber tip may form a probe for a sensor to measure changes in a reflective surface's position. Some fiber-optical interferometers for displacement measurements use a fiber probe with a sensing facet that is perpendicular to the fiber core. A reflective surface whose displacement is under measurement ("measurand surface") is generally oriented perpendicular to the fiber core. The fiber end facet and the reflective measurand surface form a Fabry-Perot cavity with the cavity optical axis along the fiber core. The output of this cavity is coupled back to the fiber and is sent to a photodetector for measurements. See U.S. Pat. No. 5,017,010 to Rugar et. al.

SUMMARY OF INVENTION

This application relates to optical fiber devices, and more specifically, to devices and sensing techniques using optical fibers to couple radiation energy.

Optical fibers can be used to guide and transmit optical signals. An optical fiber may include a high-index fiber core surrounded by a lower-index fiber cladding. This structure can confine the majority of energy of a guided optical mode within the fiber core and guide the optical energy to propagate along the fiber core through total internal reflections at the boundary of the fiber core and the fiber cladding. One method of coupling an optical signal into and out of a fiber is coupling along the fiber core axis. One distal end of the fiber may have a polished facet normal to the fiber axis to allow transmission of light out of the fiber along the longitudinal direction of the fiber core.

Since a fiber is compact in size and is mechanically flexible, it can be deployed in various environments to deliver and receive light where traditional light-guiding optical elements may be inconvenient or even infeasible. For example, a fiber may be directly coupled to a semiconductor diode or a semiconductor substrate containing optoelectronic circuits to receive light and deliver the received light to a desired destination. A fiber with an oblique-angle-polished end facet has been used to couple optical energy via evanescent fields through the angle-polished facet. See Ilchenko et. al., Optics Letters, vol. 24(11), pp. 723, 1999.

Optical fibers can also function as probes to collect optical signals for various sensing purposes. For example, a fiber tip may form a probe for a sensor to measure changes in a reflective surface s position. Some fiber-optical interferometers for displacement measurements use a fiber probe with a sensing facet that is perpendicular to the fiber core. A reflective surface whose displacement is under measurement ("measurand surface) is generally oriented perpendicular to the fiber core. The fiber end facet and the reflective measurand surface form a Fabry-Perot cavity with the cavity optical axis along the fiber core. The output of this cavity is coupled back to the fiber and is sent to a photodetector for measurements. See U.S. Pat. No. 5,017,010 to Rugar et. al.

BRIEF DESCRIPTION OF DRAWINGS

Like reference symbols in the various drawings indicate like elements.

DETAILED DESCRIPTION

Optical coupling into and out of a fiber can be achieved in a direction perpendicular to the fiber core in a transverse coupling mode. Such transverse coupling may be implemented through direct light propagation or through evanescent fields. The following describes various devices which utilize such transverse fiber coupling to achieve certain operational and device design advantages.

Figure 1:
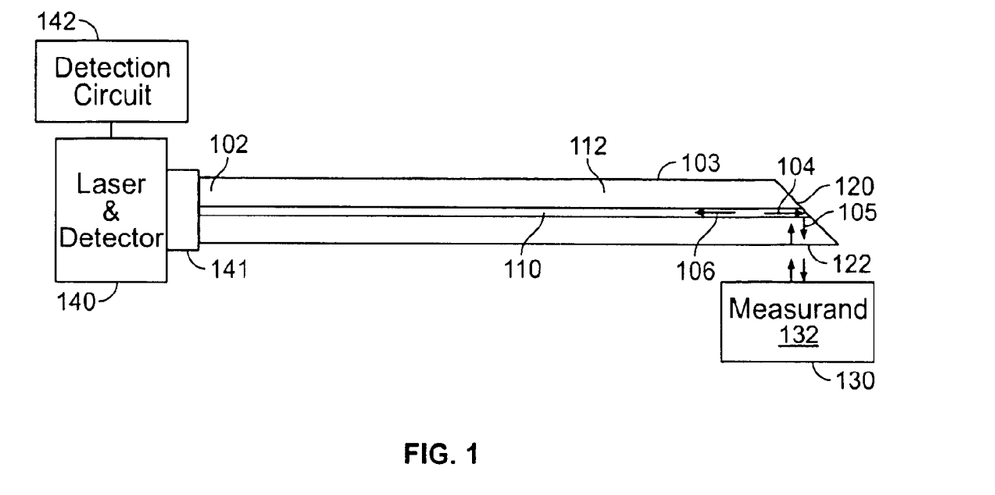
FIG. 1 shows one embodiment of a transverse fiber-optic interferometer.

FIG. 1 shows one embodiment of a fiber-optic interferometer 100 in the transverse coupling mode to measure a measurand surface 130, which is at least partially reflective. A fiber 101 with a fiber core 10 and cladding 112 has a first distal end 102 and a second distal end 103. A single mode or multimode fiber may be used. The first distal end 102 is coupled to a laser and detector unit 140 through a coupler 141 to send an input beam 104 to the second distal end 103 and to receive an output signal 106 from the second distal end 103. A detection circuit 142 receives and processes an output from the detector to determine the spacing between measurand surface 130 and the second distal end 103. The second distal end 103 has an end facet 120, which forms an angle with respect to the fiber core 110. The plane of the end facet 120 should intersect the plane of the measurand surface 130 in a line perpendicular to the fiber core 110.

In general, the angle of the end facet 120 may be at or near 45 degrees with respect to the fiber core 110 so that the reflected beam 105 from the facet 120 is substantially perpendicular to the fiber core 110. To ensure a nearly total reflection with a minimum loss at the end facet 120, the end facet 120 may be coated with a metallic film or multiple dielectric layers to be reflective. Alternatively, the index of refraction of the core 110 may be sufficiently large so that the critical angle for the total internal reflection from the fiber core to the air is less or equal to 45 degrees. For example, many fiber cores are formed of a glass with an index about 1.5 to have a corresponding core-air critical angle of about 41.8 degrees, less than 45 degrees.

The end facet 120 may be a flat surface as illustrated or a non-flat surface. The profile of the non-flat facet 120 may be designed to modify the properties of the beam, such as the beam focus or collimation. The non-flat facet 120 may be cylindrical, spherical, or a combination of multiple polished planar facets.

The reflected beam 105 from the end facet 120 transmits through a side surface 122 of the cladding 112 to illuminate the measured surface 130. Since both the measurand surface 130 and the side surface 122 of the fiber 101 are at least partially reflective, these two surfaces form a Fabry-Perot optical cavity. The optical axis of this cavity is essentially perpendicular to the fiber core 110. The cavity length is the spacing between the side surface 122 of the fiber 101 and the measurand surface 130. The transverse-reflected beam 105 enters the cavity from the side surface 122 and bounces one or more times within the cavity before exiting as an output beam 106. The output beam 106 primarily includes the interference field at the side surface 122 between a first reflected beam by the side surface 122 and a second reflected beam from the measurand surface 130. Hence, the angled distal end 103 and the measurand surface 130 form an optical interferometer.

In operation, the transverse interferometer 100 measures the variation in the intensity of the output beam 106, which depends on a change in the relative position between the measurand surface 130 and the side surface 122. The intensity of the output beam 106 varies approximately according to a sinusoidal function of the phase shift of a round trip within the cavity. A maximum intensity in the beam 106 is obtained at each of multiple spacings, which are separated by a phase shift of 360 degrees, or a path length difference of one half of the optical wavelength. Since the intensity variation is most sensitive to the spacings where the slope of the sinusoidal function is the greatest, the initial spacing between the side surface 122 and the measurand surface 130 may be biased at such a position. In one implementation, the fringe visibility in the output-beam 106 is measured to be greater than 30%, and the tolerance to misalignment of the fiber polish plane relative to the measured surface is 1–3 degrees.

The coupler 141 may be a fiber coupler with one or more coupling ports. When the coupler 141 is a multi-port coupler, a multiple fibers like the fiber probe 101 may be attached thereto so that multiple interferometric signals from the fiber probes can be sent to the detector in 140.

Figure 1A:
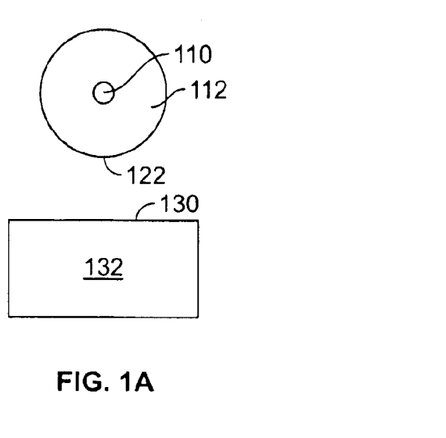
FIGS. 1A and 1B show two exemplary configurations for a side surface through which optical energy is coupled to and from a measurand surface in the interferometer 100 of FIG. 1.
Figure 1B:
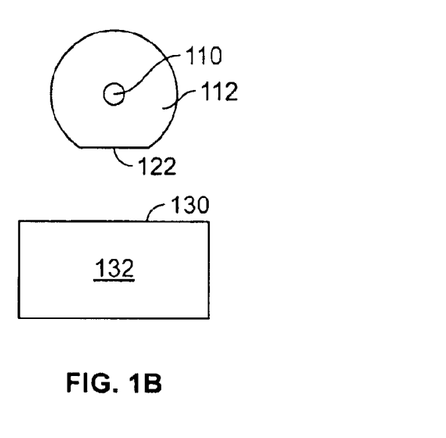

FIGS. 1A and 1B show two exemplary configurations for the side surface 122 in the transverse fiber interferometer 100 of FIG. 1. In FIG. 1A, the side surface 122 of the fiber 101 is a cylindrical surface; which can operate as a cylindrical lens. A beam passing through the side surface 122 is focused along a direction perpendicular to the fiber core 110. Alternatively, at least a portion of the side surface 122 in the optical path of the beam 105 or 106 may be flat as shown in FIG. 1B. In general, the surface profile of the side surface 122 may be designed in various configurations to modify the focus properties of the light coupled into or out of the fiber. The designs of the surface profiles of the end facet 120 and the side surface 122 may be associated with each other to achieve efficient coupling.

Figure 2A:
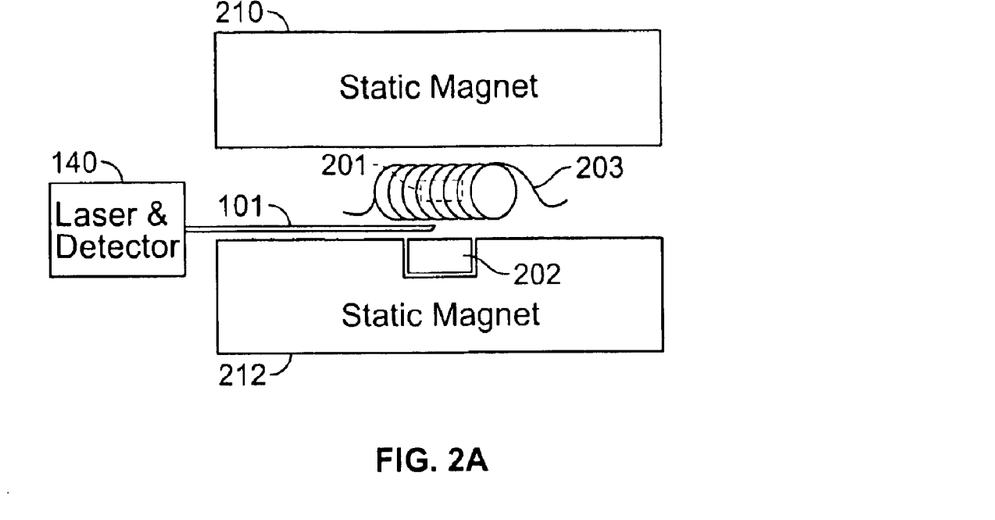
FIGS. 2A and 2B show two exemplary applications of the transverse fiber interferometer of FIG. 1.

The transverse fiber interferometer 100 may be deployed in environments that have limited space or geometric constraints for receiving a sensing device. FIG. 2A shows one exemplary application of such a transverse fiber interferometer in a force-detected magnetic resonance spectrometer. A magnetized movable sample 201 or a movable sensing magnet 202 is located in a RF excitation coil 203 with a narrow gap between permanent magnets 210 and 212. The total magnetic field at the sample 201 is substantially homogeneous without a field gradient. The fiber probe 101 with the angled end surface 120 of the transverse fiber interferometer 100 can be inserted in various gaps between the magnets to measure the movement of either the sample 201 or the sensing magnet 202. Alternative to the magnet configuration for magnets 212 and 202, the magnet 212 may have a flat surface and the magnet 202 is placed above that flat surface with a gap therebetween. The fiber probe 101 can be inserted in this gap to measure the movement of the magnet 202.

In such an instrument, it would be difficult to deploy a conventional fiber interferometer, which couples light longitudinally along the fiber axis to a measurand surface because portions of the magnets would need be removed to allow insertion of a fiber probe parallel to the static magnetic field. Hence, the design and performance of this spectrometer may by detrimentally affected.

Notably, since the fiber core 110 is essentially parallel to the measurand surface 130, the position of the second distal end 103 with angled end facet 120 can be externally modulated to oscillate perpendicular to its own axis. A positioning element may be used to control and modulate the position of the second end 103 relative to the measurand surface 130. In one implementation of the positioning element, one or more layers of piezoelectric material and electrodes may be deposited onto the surface of the second distal end 103 of the fiber 111 opposite from and parallel to the measurand surface 130 so that the fiber s distance from the measurand surface 130 may be adjusted or fed back without attachment of any extrinsic piezo actuators. This mechanism may provide a harmonic modulation of the light signal in addition to the modulation caused by the movement of the measurand surface 130. This could be utilized in applications where the fiber is itself driven in proportion to the quantity to be measured, or the fiber forms a mechanical element of the sensor. The reflective surface 130 external to the fiber 101 may in this case function as a point of reference for monitoring the change of position of the fiber probe. For example, the fiber may be used as a mechanical oscillator in a MEMS device or a force microscope. This modulation control of the fiber end can also be used to shift low-frequency or DC detected signals to higher frequencies in order to reduce noise. The fiber probe hence may be used to deliver a probe beam to a surface, modulate the return probe light in proportion to the measured quantity, and direct the modulated light to a receiver coupled to the first distal end 102 of the fiber 101.

Figure 2B:
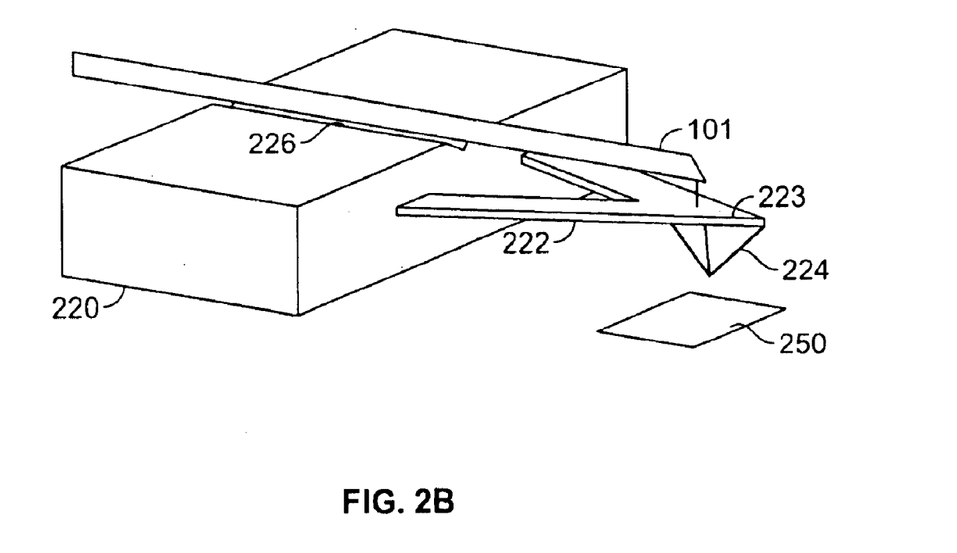

FIG. 2B shows another exemplary application of the transverse fiber interferometer in an atomic force microscope (AFM). The sensing module for the AFM includes a substrate 220 (e.g., a silicon substrate). A mechanical cantilever 222 is formed from or attached to the substrate 220 and has a reflective tip portion 223 to hold a sensing probe 224. The fiber probe 101 may be engaged to the substrate 220 so that the second distal end 103 with the angled end facet 120 is positioned over the tip portion 223. In operation, a sample 250 is placed under the sensing probe 224. The atomic interaction between the sample 250 and the probe 224 causes a change in the position of the probe 224. This position change is then measured from the intensity variation in the reflected beam from the tip portion 223. This approach to position sensing may be applied to other force microscopes or sensors which employ cantilevers or other mechanical oscillators for measurement.

Force-detected instruments, such as AFM, NMR, and other force microscopes, require positioning and aligning a fiber probe or other displacement sensor to within microns of the mechanical oscillator and feedback on the average spacing between the fiber probe and the oscillator, i.e., the cavity path length, to submicron tolerances. Use of the transverse-fiber interferometer would eliminate stabilization of the fiber tip in 2 dimensions. A groove (e.g. a V-groove) 226 can be formed in the substrate 220 in the system of FIG. 2B to hold the fiber probe 101 fixed perpendicular to the fiber axis. The fiber probe 101 can then be aligned and fixed in the second dimension, along its fiber core axis. In the third dimension, along the optical cavity axis, the fiber may not require stabilization if the groove is micromachined accurately enough to hold the fiber at a position of steep fringe slope to allow sensitive interferometry. Without the required micromachining accuracy, a piezoelectric actuator, coated onto the fiber or otherwise, may be used to feedback on or align the fiber along the cavity axis.

In the above optical measurement applications, many transverse fiber-optic probes may be coupled through a multi-port fiber coupler to a single laser and a single photodetector to achieve efficient multiplexing of detected signals and reduce device complexity.

Coupling light transverse to a fiber using an angled end facet can also form a compact fiber optical head for reading and writing in optical disk drives (e.g. CD' or DVD') or in other optical data storage devices. Such a fiber optical head can simplify the head design, reduce the manufacturing cost, and improve the performance of the disk drives. Fibers are capable of carrying sufficient power, on the order of 10–100 mW, to accomplish both-reading and writing operations on an optical disk.

Figure 3:
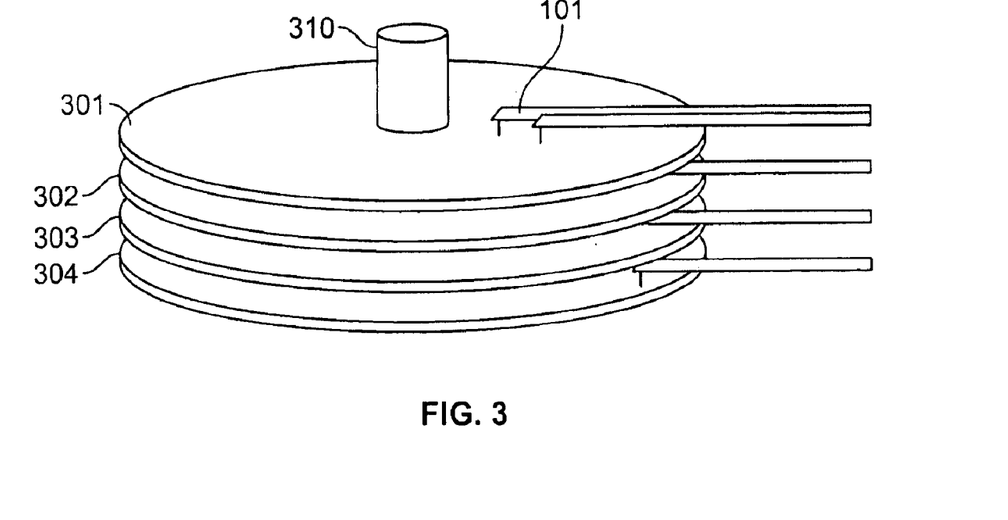
FIG. 3 shows an optical disk drive using one or more transverse fiber probes to replace conventional optical read and write heads.

FIG. 3 shows an optical disk drive 300 with multiple optical disks, 301 through 304, engaged to a common motorized spindle 310. Multiple optical heads based on the above transverse fiber probe are used to interact with different disks. Each optical head includes a fiber probe 101 with an angled end facet to couple light to and from the disk in a direction perpendicular to the fiber core 110. A fiber optical head can be engaged to a head actuator to control the position of the head over a disk during reading or writing operations. The fiber optical head may be placed within microns of the disk surface. Since each fiber probe is small, many optical disks can be closely stacked on the spindle 310 while one or more fiber optical heads can be placed between each pair of adjacent disks. In one implementation, the fiber optical heads may be controlled to access all disks on the spindle simultaneously to achieve a high data rate. Each disk may be configured to have recording layers on both sides and at least two fiber optical heads, one on each side, to access the data. Two or more fiber optical heads may also used to respectively access two or more different recording layers on one side or both sides of each disk. Such fiber optical heads can be used to achieve small spacings between disks and hence compact multi-disk accessing systems that are not possible with conventional optical heads.

Figure 4A:
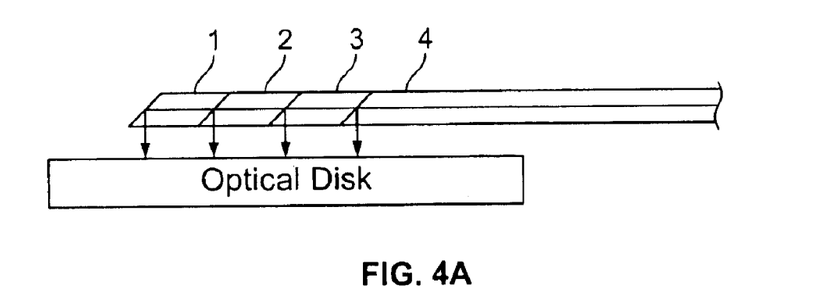
FIGS. 4A and 4B show different views of a multi-head module with multiple transverse fiber tips for fast data accessing.
Figure 4B:
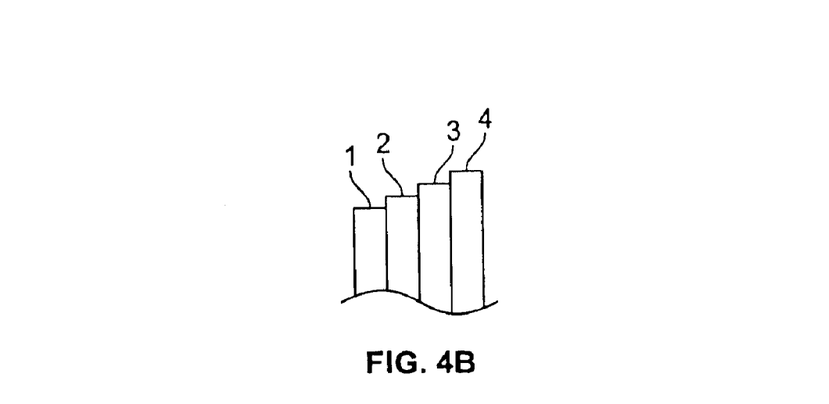

Multiple fiber optical heads can also be used to form a multi-head fiber module to read or write different data tracks in parallel in the same recording layer on one side of each disk. FIGS. 4A and 4B show a side view and a top view of such a multi-head fiber module to achieve a high data rate. Multiple fiber heads are joined to one another to form a planar fiber array for reading or writing a single disk. The tip of each fiber head is displaced relative to an adjacent fiber head to read different tracks on a disk at the same time. This multi-head fiber module can be used to achieve a high data rate but a low disc rotation speed since multiple tracks are accessed at the same time by different heads. The combination of many fiber optical heads per disk, and many closely spaced disks on a spindle allows for compact, high-density optical disk drives capable of extremely high data rate. Two different fiber heads may be coupled to a common laser source and a photodetector.

Multiple transverse fiber probes can also used in an optical disk drive to control the positioning of an optical head relative to a disk surface. Some-optical disk drives split a laser into more than one beam to maintain the lateral tracking of the read/write head and ato maintain its distance from the disc. The transverse fiber sensor system may accomplish this by using 2 or 3 parallel fibers, each of which sends and detects a laser beam. Feedback on the read/write fiber tip position may be accomplished by use of one or more reference beam signals.

In the above optical disk drive applications, many fiber heads may be coupled through a multi-port fiber coupler to a single laser and a single photodetector to achieve efficient multiplexing of signals and reduce device complexity.

Figures 5, 5A:
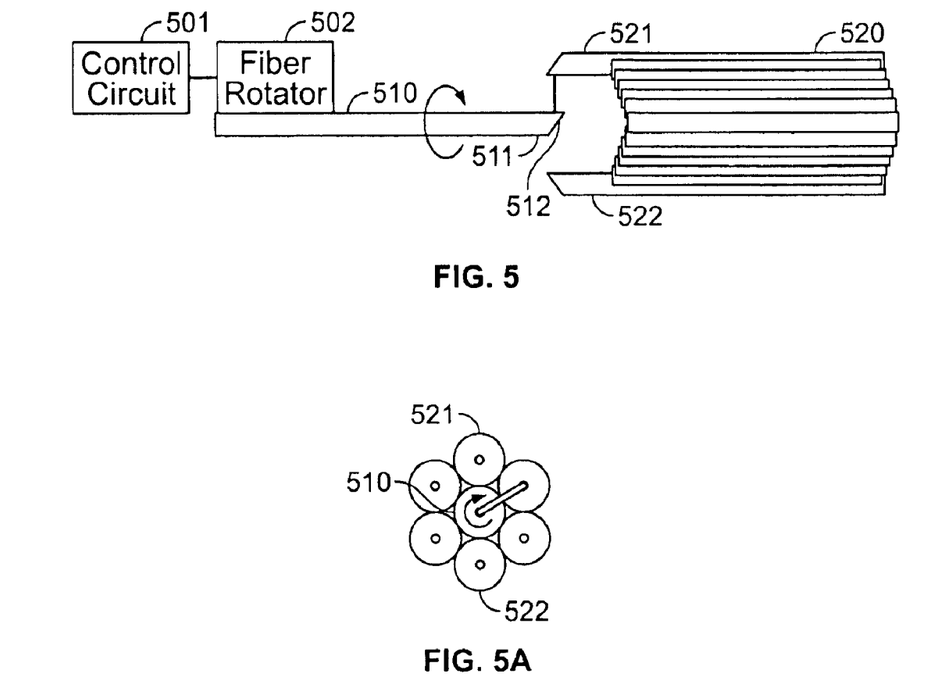
FIG. 5 shows a 1xN optical fiber switch formed of multiple fibers with angled end facets for transverse coupling.
FIGS. 5A and 5B show two examples for a circular arrangement of a rotary optical switch fiber bundle.

Optical switching for data transfer and networking may also be accomplished using transverse light coupling from angle-polished fibers. FIG. 5 shows one embodiment of an optical fiber switch 500 using a plurality of transverse fiber probes. The fiber switch 500 includes a single fiber 510 and a fiber bundle 520 with multiple fibers (e.g., 521 and 522). The single fiber 510 has a light-switching terminal 511 with an angled end facet 512 similar to the construction of the second distal end 103 of the fiber probe 101 in FIG. 1. The fiber bundle 520 has a first side that is positioned relative to the light-switching terminal 511 of the single fiber 510 so that each fiber in the fiber bundle 520 can establish an optical link with the single fiber under a desired condition.

Figure 5B:
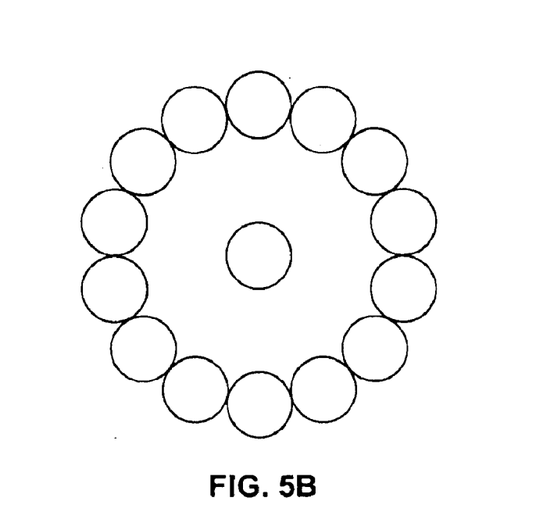

The fibers in the fiber bundle 520 are arranged to have their distal ends in a common plane surrounding a common point, where the single fiber distal end 511 resides. Each fiber distal end in the common plane has an angled end facet that faces radially away from the common point. The fibers are arranged such that an unbroken straight line can be connected between the single fiber end 51 and any other distal end in the fiber bundle 520. In one implementation, the distal end 511 of the single fiber 510 is located in the common plane of the first end of the fiber bundle 520. The fiber bundle distal ends may be symmetrically located with respect to the fiber end 511. For example, the fiber bundle distal ends may be located on the circumference of a circle with the single fiber end 511 at the center of that circle. FIG. 5A shows that the fiber bundle 520 is formed of six fibers in a circular pattern. FIG. 5B shows the fiber bundle 520 is formed of more than six fibers.

In operation, the single fiber 510 changes its orientation with respect to the fibers in the fiber bundle 520 in order to direct a light beam to, or receive a light beam from, different distal ends of the fiber bundle 520. In FIG. 5, the single fiber 510 is rotated to a position to optically link with the fiber 521 in the fiber bundle 520. FIG. 5A shows that the single fiber 510 can turn to switch to a fiber next to the fiber 521. Therefore, the device 500 operates as a rotary 1xN optical switch if there are N fibers in the fiber bundle 520.

A fiber rotating mechanism 502 may be coupled to either the single fiber 510 as shown or the fiber bundle 520 to rotate the single fiber 510 relative to the fiber bundle 520. A control circuit 501 may be used to control the relative angle of the single fiber 510 with respect to the fiber bundle 520. The control circuit 501 can command the beam carried in the single fiber 510 to be switched to any one of the fibers in the fiber bundle 520 or vice versa.

Figure 5C:
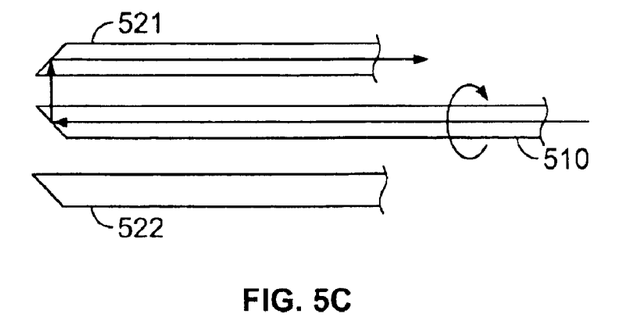
FIG. 5C shows another embodiment of a 1xN rotary optical fiber switch.
Figure 5D:
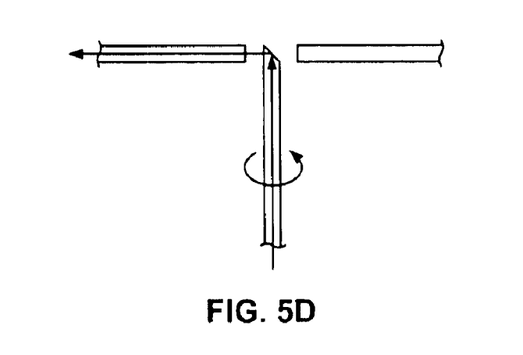
FIGS. 5D and 5E show another embodiment of a 1xN rotary optical fiber switch.
Figure 5E:
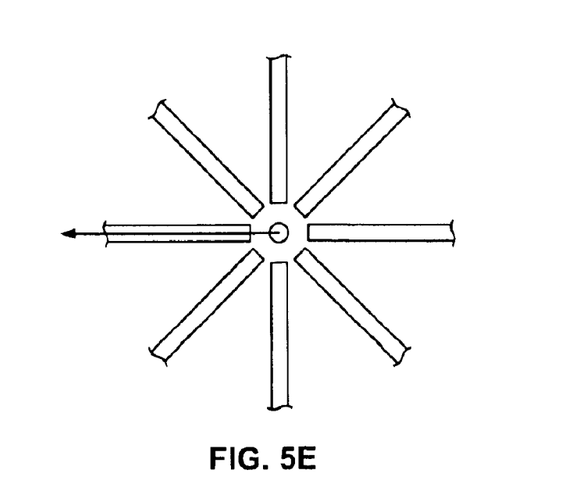

The embodiment in FIG. 5A positions the single fiber 510 separately from the fiber bundle 520 except that the switching end 511 is located in the common plane of the distal ends of all fibers in the fiber bundle 520. Alternatively, as illustrated in FIG. 5C, the single fiber 510 may be placed in the center of the fiber bundle 520 to perform the switching operations. FIGS. 5D and 5E show another 1xN rotary optical fiber switch in which a single fiber 510 with an angled end facet 511 is used to switch signals into a fiber array with multiple fibers (e.g., 531 and 532). The fibers 531 and 532 in the fiber array are arranged in a common plane such that the distal ends of the fibers are pointed to a common location. These fibers have end facets that are perpendicular to their fiber axes. The single fiber 510 is substantially perpendicular to the common plane and its angled end facet 511 is positioned at the common location to optically communicate with each fiber in the fiber array at a different orientation. The end facet of the distal end of each fiber is either substantially perpendicular to the fiber or has a small angle with respect to the fiber core to receive an optical beam from the angled end facet 511 of the single fiber 510. FIG. 5D shows the side view in a plane perpendicular to the fiber array. FIG. 5E shows the view in the plane of the fiber array. A circular arrangement of the fiber array is shown where the angled end facet 511 is at the center of the circle.

In other embodiments, both the end facets of the single fiber 510 and the fiber bundle 520 may have different polish angles or curvature patterns to achieve optimal light coupling between them, or to tailor geometric design parameters. Using different polish angles and patterns allows for designs with non-coplanar positions of the fiber bundle 520 distal ends and the single fiber distal end 511. It may also be advantageous to use multi-mode or single-mode fibers with different core sizes or material properties within the switch to attain desired light coupling properties for various applications.

One notable feature of the above 1xN fiber switch is its simplicity in structure. N can be relatively large without significantly increasing the physical dimension of the switch. In addition, two or more such fiber switches may be coupled together to perform complex switching operations.

Wavelength-division multiplexing (WDM) in the described optical switches may be accomplished by using several wavelengths of light in the fibers. The distal end facet 511 of the single fiber 510 may be used to spatially separate different wavelengths of a WDM signal. The facet 511 may be etched or coated to form a diffraction grating. Alternatively, no diffraction grating may be needed since the angle-polished end 511 of the fiber 510 acts as a prism to spatially separate substantially different wavelengths of light.

Figure 5F:
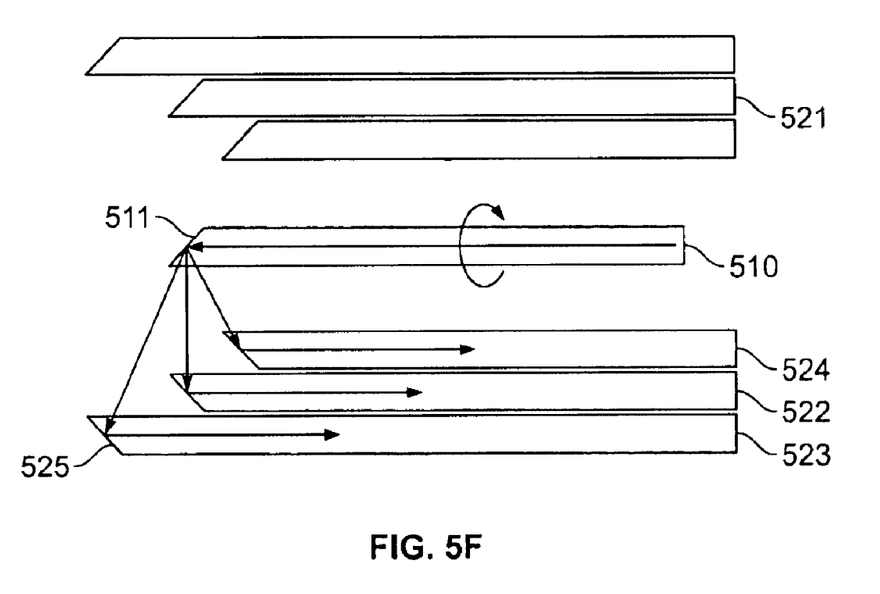
FIG. 5F shows another embodiment of a 1xN rotary optical fiber switch.

FIG. 5F shows a side (cross-sectional) view of one embodiment of such a WDM switching device. The receiving fibers, 521 through 524, are concentric rings of fiber bundles 520, with each ring having its distal ends in different planes. Light of multiple wavelengths carried by the fiber emerges at different angles from the central fiber distal end after striking the end facet, which incorporates a diffraction grating. Concentric receiving fiber bundles 520 are placed such that their distal-end common planes are aligned to receive different angles, or wavelengths, of light from the central fiber 510.

Other applications of the transverse fiber tip are envisioned. For example, medical microsurgery, tissue ablation, angioplasty, and endoscopic measurements currently utilize lasers and fiber-optics tools. The transverse-fiber tip allows conveniently manufactured flexibility in the direction that light is launched relative to the fiber axis. Optical coherence tomography (OCT) and laser tissue coagulation, cauterization, or ablation are applications where fibers are used in combination with extrinsic prisms, mirrors, or lenses to direct light from a fiber transverse to the fiber axis. See U.S. Pat. No. 5,321,501 to Fujimoto et. al., and Prostenko et. al., Adult Urology, 47(6) 1996, respectively. Light may be more efficiently directed at arterial walls in which the fiber is inserted to blast away plaques, or to perform profilometry, imaging, or spectroscopy on the vessel walls.

As another example, micromachining processes rely on devices built and implemented on a 2-dimensional wafer. Many micro-electromechanical system (MEMS) devices require sensitive displacement measurements of microscopic moving parts. As MEMS devices are made smaller and device density increases, wafers will be stacked close to each other to produce 3D arrays of devices. The present transverse fiber tip can be intercalated into these arrays with less device disruption or re-design than a normal fiber interferometer would require.

In addition, the transverse fiber tips may be used as in-situ sensors to monitor film thickness, strain, or device features during fabrication processes such as CVD, deep reactive-ion etching, wet etching, or electroplating. A transverse fiber may be laid into a V-groove that is part of, or is fixed to, a substrate or wafer undergoing processing so that the fiber is accurately positioned relative to the device features. This accurate positioning would be similar to that described above for the AFM embodiment. Fibers may then be slid in and out of a film growth or etching chamber during the fabrication process with <250 nm reproducibility and minimal effort. Alternatively, the fiber may be fixed in place relative to the substrate during the process. As in the fiber optical disk heads, multiple-fiber probes may be used as reference probes to control accurate fiber positioning relative to a substrate. Affordable measurements, or metrology, of MEMS and integrated circuits during fabrication processes can be critical to achieving high throughput, yield, and efficiency.

Another aspect of the present disclosure is a fiber position sensor based on optical interference and transverse coupling via evanescent fields. One embodiment of such a fiber position sensor uses the distance-dependent change in absorption, refraction, or reflection by an object to be measured. The light is transversely coupled outside the core of a single-mode optical fiber via evanescent fields. The electric field of the evanescent wave decays exponentially from the surface of a fiber core into the surrounding medium. A strongly light absorbing material is coated onto a surface of the object to be measured, which lies parallel to the fiber axis. The optical power absorbed by the object s surface depends on the distance between the fiber and the substrate. Alternatively, optical power may, be coupled away from the fiber by distance-dependent refraction or reflection by the substrate.

Figure 6:
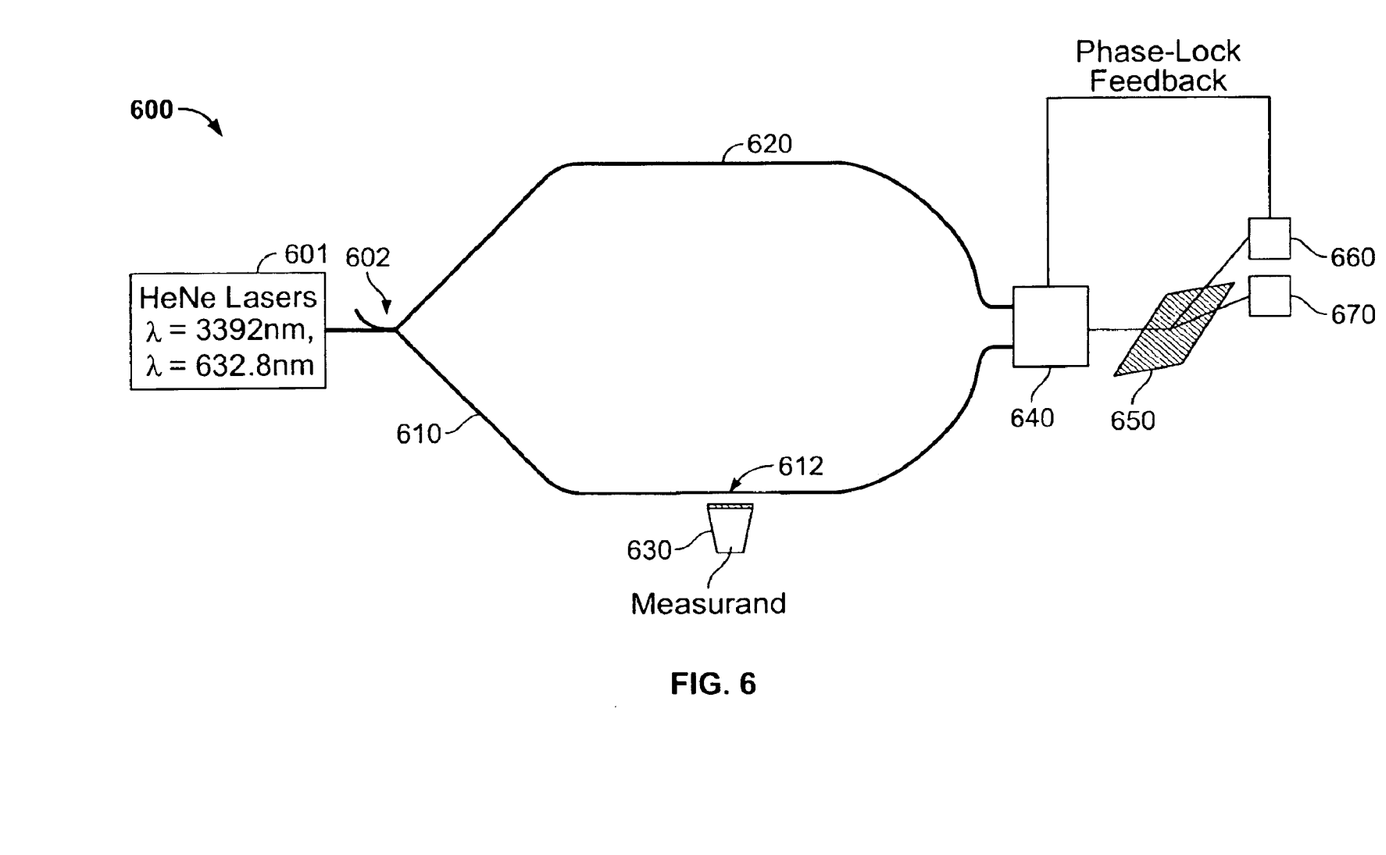
FIGS. 6, 6A and 6B show a fiber position sensor based on transverse evanescent-field coupling.
Figure 6A:
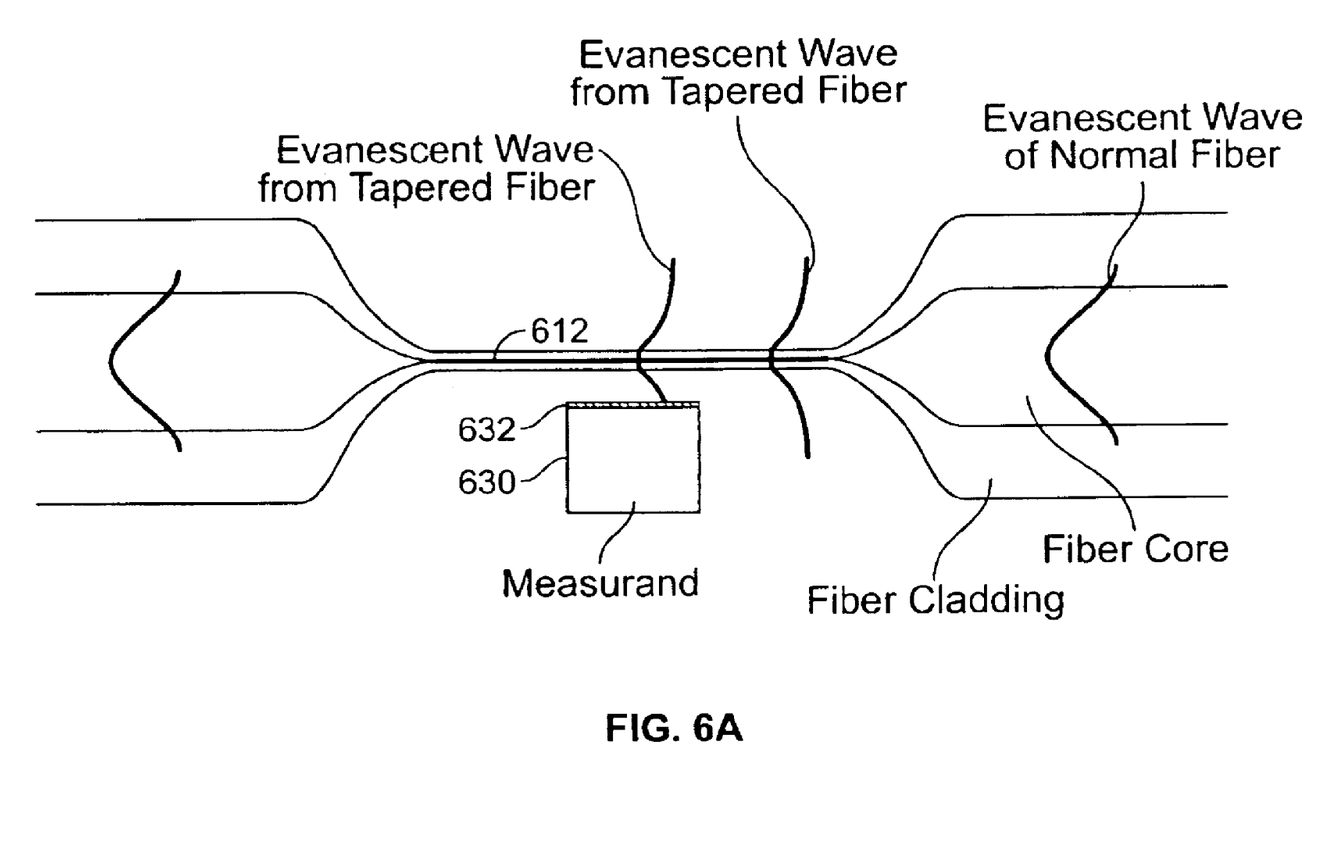

FIG. 6 shows one embodiment of such a fiber position sensor 600 to measure changes in the distance between the fiber surface and the measurand surface 630 parallel to the fiber axis. The fiber position sensor 600 includes a signal fiber 610 and a reference fiber 620. A signal laser is divided into two equal parts, which are respectively coupled to the fibers 610 and 620. The signal fiber 610 includes a tapered sensing region 612 with a reduced diameter compared to rest of the fiber so that the evanescent power output of the tapered region 612 is sufficiently high for the measurements, e.g., about 40% of the total signal laser in the signal fiber 610 may be in the evanescent wave outside the fiber core in the tapered sensing region 612 (FIG. 6A). The evanescent wave decays exponentially from the surface of the tapered sensing region 612. The measurand surface 612 is designed to absorb the signal laser. For example, an absorptive polymer layer 632 may be coated on the measurand surface 630 if the original measurand surface 630 does not absorb the signal laser.

The signal and reference fibers 610 and 620 are optically coupled at their output ends and are designed to cause a phase delay of 180 degrees so that there is interference between the signal beams from the two fibers. Hence, if the optical intensities of the laser signal beams out of the two fibers 610 and 620 are the same, the intensity of the combined output is zero. This happens when the signal and reference fibers 610 and 620 are properly designed and when there is no absorption of the evanescent wave at the sensing region 612. When an absorbing measurand surface 630 is placed within the evanescent field in the tapered sensing region 612, the output intensity is no longer zero even if the relative phase delay is maintained at 180 degrees. Phase differences in the two paths and their variation with the position of the measurand may also be extracted from the signal.

Hence, the optical intensity of the combined output indicates the amount of absorption and/or dispersion by the measurand surface 630 at the tapered sensing region 612 if the relative phase delay between the signal and reference fibers 610 and 620 is maintained at 180 degrees. Since the amount of absorption is an exponential function of the distance between the outer surface of tapered sensing region 612 and the measurand surface 630, the measured intensity of the combined output can be calibrated to indicate the distance based on the exponential decay of the field intensity outside the tapered section 612.

The proper operation of the fiber sensor 600 is based on the condition that the relative phase delay between the signal and reference fibers 610 and 620 is maintained at 180 degrees for each measurement. However, environmental and other factors such as temperature, vibrations, stresses, bending of the fibers, aging of the fibers, and others may affect the optical pathlength of either of the signal or reference fibers 610 and 620. Hence, a phase-lock mechanism is implemented to actively maintain the relative phase delay by using a separate reference interference measurement.

The fiber position sensor 600 uses a light source 601 to produce two separate output laser beams at two different wavelengths: the signal beam and an additional reference beam. A. 50/50 fiber coupler 602 is used to divide each laser beam into two equal parts for the two fibers 610 and 620. The signal beam may have a signal wavelength much longer than that of the reference beam so that the reference beam is essentially confined within the tapered sensing region 612 and is not absorbed by the measurand surface 630 while a significant portion of the evanescent field of the signal beam is outside the tapered sensing section 612. Under this condition, the interference of the two reference beams in the signal and reference fibers 610 and 620 is an indication of the relative phase delay and is not affected by the presence of the measurand surface 630. Any change that affects the relative optical path length difference between the two fibers can then be monitored based on the interference pattern of the combined reference beam output. The phase-lock mechanism can be used to lock the relative phase difference for the signal beam at 180 degrees or another desired value by controlling the optical path length of at least one of the fibers 610 and 620 according to the interference signal of the reference beams.

In the implementation shown in FIG. 6, the phase-lock mechanism includes a phase-lock element 640 operable to adjust the phase difference in response to a feedback signal. A diffraction grating 650 or other wavelength-selecting element is used to separate the combined reference output and the combined signal output. A reference detector 660 receives and converts the combined reference output into the feedback signal. Another signal detector 670 is disposed to measure the combined signal output to determine the spacing between the measurand surface 630 and the outer surface of the tapered sensing region 612.

Figure 6B:
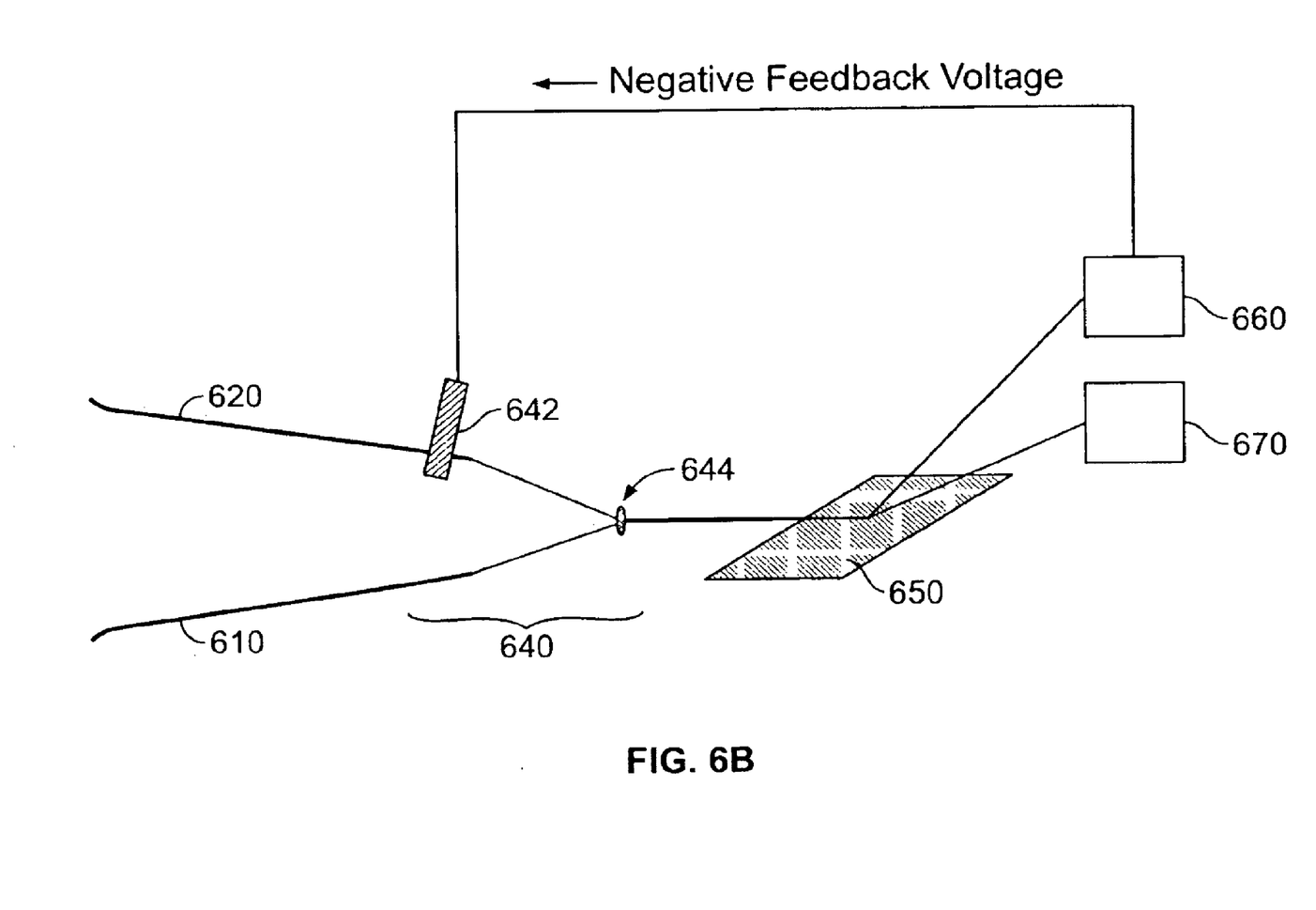

FIG. 6B shows one example of the phase-lock element 640 which includes a piezoelectric feedback positioner 642 and an aperture 644. The positioner 642 is coupled to the reference fiber 620 to change the distance between the distal end of the fiber 620 and the aperture so as to adjusts the phase delay in the reference fiber 620. The aperture 644 combines the beams from the fibers 610 and 620 together for interference measurements. Alternatively, the positioner 642 may be replaced by a fiber stretcher or other fiber phase-modulation device.

As an example, the light source 601 may include two He-Ne lasers which respectively produce a signal beam at 3392 nm and a reference beam at 632.8 nm. The tapered sensing region 612 may be on the order of 5 mm long where the fiber s diameter is reduced to less than 2 microns. The measurand surface 630 is placed approximately 1 micron from the tapered sensing section 612. The 3392 nm light in the signal fiber 610 is absorbed by the 2 micron thick polymer coating on the surface of the measurand, where the strength of this absorption is dependent on the distance of the measurand from the fiber surface.

The combination of the 3392 nm signal and reference beams effectively subtracts their intensities providing that these waves are held 180 degrees out of phase with each other. This intensity subtraction results in a signal which is proportional only to the evanescent-wave power absorbed by the measurand, and thus the photon shot-noise, which is the main noise source in this device, is reduced. At other relative phases, a similar sensitivity is achieved since the interference signal and the shot noise grow similarly. After combination of the 3392 nm signal and reference beams at the phase-locked fiber coupler, this light is directed by the diffraction grating onto photodetector 2. The voltage out of photodetector 2 is proportional to the power absorbed by the measurand and thus varies exponentially with the measurand s displacement, or varies approximately linearly for small displacements.

For a tapered section of 2 microns in diameter, the cut-off wavelength is 2.6 microns, above which the fiber is single-mode. Thus the tapered fiber is single-mode at the 3392 nm wavelength, and all of the power put through the signal fiber passes in the fundamental mode of the fiber, which eliminates higher mode coupling effects. Due to the small diameter of the taper, the exponentially decaying evanescent-wave surrounding it carries a large fraction of the light power guided by the fiber. The portion of this evanescent-wave that hits the polymer layer will be absorbed almost completely, providing the polymer is strongly absorbing at 3392 nm.

Multiple tapered sensing regions 612 may be employed on a single signal fiber 610 in order to make multiple position measurements. In general, the position measurements could be made on multiple measurands 630 oscillating at different frequencies in order to separate and identify the interferometric signals corresponding to the different measurands. Alternatively, the positions of tapered sensing regions 612 themselves could be modulated relative to the measurands 630 to shift the frequencies of the different interferometric signals relative to one another.

The above fiber position sensor 600 can be used in various position sensing applications as the transverse fiber interferometer shown in FIG. 1.

A number of embodiments have been described. Nevertheless, it will be understood that various modifications and enhancements may be made without departing from the spirit and scope of the following claims.

What is claimed is:

1. A device, comprising:
  a reference fiber having a first terminal and a second terminal;
  a signal fiber having a first terminal and a second terminal, and a tapered section between said first and second terminals which has a reduced dimension to allow a desired portion of a guided optical beam at a signal frequency to exist outside said signal fiber in form of an evanescent field;
  a first optical coupler to divide a signal laser beam at said signal frequency into a first signals beam and a second signal beam of an equal intensity and to couple said first and said second signal beams into said first terminals of said signal and said reference fibers, respectively;
  a second optical coupler coupled to said second terminals of said signal and said reference fibers to combine said first and said second signal beams into an output signal beam in which said first and said second signal beams are 180 degrees out of phase relative to each other;
  a measurand surface disposed adjacent to said tapered section of said signal fiber to absorb optical energy in said evanescent field; and
  a signal photodetector to receive said output signal beam from said second optical coupler to produce a detector output indicating a spacing between said measurand surface and said signal fiber at said tapered section.

2. The device as in claim 1, further comprising a phase-lock element to maintain said first and said second signal beams are at a specific phase relative to each other at said second optical coupler.

3. The device as in claim 1, wherein said phase-lock element is operable to change a phase delay in at least one of said signal and said reference fibers.

4. The device as in claim 1, wherein said phase-lock element is operable to measure an interference between two reference signal beams respectively passing through said signal and said reference fibers at a reference frequency that is not absorbed by said measurand surface to determine a relative phase change in said reference and said signal fibers, wherein said interference is measured from an output reference beam produced by said second optical coupler.

5. The device as in claim 1, further comprising a wavelength-selecting element to separate said output signal beam and said output reference beam, and a reference photodetector to receive said output reference beam.

6. The device as in claim 1, further comprising more than one of said tapered sections on said signal fiber for the purpose of observing the motion of more than one of said measurand surfaces.

7. The device as in claim 6 further comprising more than one of said measured surfaces oscillating at substantially different frequencies for the purpose of separating, in frequency, said output signal beams for each of said measurand surfaces.

8. The device as in claim 6, further comprising one or more actuators to modulate the position comprising one or more of said tapered sections for the purpose of shifting the frequencies of one or more of said output signal beams and separating, in frequency, said output signal beams for each of said measurand surfaces.

* * * * *

UNITED STATES PATENT AND TRADEMARK OFFICE
CERTIFICATE OF CORRECTION

PATENT NO.    : 6,882,429 B1
DATED         : April 19, 2005
INVENTOR(S)   : Daniel P. Weitekamp and Louis A. Madsen It is certified that error appears in the above-identified patent and that said Letters Patent is hereby corrected as shown below:

Column 1,
Line 11, please insert the following prior to the section entitled, "Background of the Invention":
-- Federally Sponsored Research or Development
     The invention described herein was made in the performance of work under a NASA contract, and is subject to the provisions of Public Law 96-517 (35 U.S.C. 202) in which the Contractor has elected to retain title. --.

Signed and Sealed this

Twenty-third Day of August, 2005

JON W. DUDAS
*Director of the United States Patent and Trademark Office*